(12) United States Patent
Planas et al.

(10) Patent No.: US 9,849,226 B2
(45) Date of Patent: Dec. 26, 2017

(54) SYSTEMS AND METHODS FOR REAL TIME CALIBRATION OF PUMP STROKE VOLUMES DURING A BLOOD SEPARATION PROCEDURE

(71) Applicant: FENWAL, INC., Lake Zurich, IL (US)

(72) Inventors: Samantha M. Planas, Wauconda, IL (US); Kathleen M. Higginson, Mount Prospect, IL (US); Amit J. Patel, Algonquin, IL (US)

(73) Assignee: Fenwal, Inc., Lake Zurich, IL (US)

( * ) Notice: Subject to any disclaimer, the term of this patent is extended or adjusted under 35 U.S.C. 154(b) by 286 days.

(21) Appl. No.: 14/577,383

(22) Filed: Dec. 19, 2014

(65) Prior Publication Data

US 2016/0175511 A1 Jun. 23, 2016

(51) Int. Cl.
- *A61M 1/36* (2006.01)
- *F04B 43/12* (2006.01)
- *A61M 1/10* (2006.01)
- *G01F 25/00* (2006.01)

(52) U.S. Cl.
CPC ........ *A61M 1/3607* (2014.02); *A61M 1/3609* (2014.02); *A61M 1/3663* (2013.01); *F04B 43/12* (2013.01); *A61M 1/1006* (2014.02); *A61M 1/1037* (2013.01); *A61M 1/1039* (2014.02); *A61M 1/1086* (2013.01); *A61M 2205/3331* (2013.01); *A61M 2205/3334* (2013.01); *A61M 2205/502* (2013.01); *G01F 25/0092* (2013.01)

(58) Field of Classification Search
CPC .............. A61M 1/1039; A61M 1/3607; A61M 1/3663; A61M 2205/3334; G01F 25/0092
USPC ................................................. 210/137, 741
See application file for complete search history.

(56) References Cited

U.S. PATENT DOCUMENTS

| | | |
|---|---|---|
| 5,733,257 A | 3/1998 | Sternby |
| 5,932,103 A | 8/1999 | Kenley et al. |
| 6,280,634 B1 | 8/2001 | Shah et al. |
| (Continued) | | |

FOREIGN PATENT DOCUMENTS

| | | |
|---|---|---|
| EP | 0723463 B1 | 3/2001 |
| EP | 0846470 B1 | 9/2003 |
| (Continued) | | |

*Primary Examiner* — Dirk Bass
(74) *Attorney, Agent, or Firm* — Cook Alex Ltd.

(57) ABSTRACT

A method is provided for the real time calibration of a pump that is part of a reusable hardware component having a programmable controller during a blood separation procedure where fluid is flowed through a tubing in a tubing set by action of the pump. The method comprises programming the controller with a continuous function defining a relationship between pump inlet pressure and pump stroke volume; commencing the fluid processing procedure to operate the pump to draw fluid through the tubing; measuring fluid pressure in the tubing at the inlet of the pump; calculating a current pump stroke volume with the controller based on the continuous function and the pump rotational rate; and adjusting the pump rotational rate utilized by the controller to control the procedure to achieve a target fluid flow rate. The continuous function defining the relationship between pump inlet pressure and the pump stroke volume may be empirically determined over a predetermined range of inlet pressures.

15 Claims, 6 Drawing Sheets

(56) References Cited

U.S. PATENT DOCUMENTS

| | | |
|---|---|---|
| 6,691,047 B1 | 2/2004 | Fredericks |
| 6,890,157 B2 | 5/2005 | Pfeil et al. |
| 6,984,218 B2 | 1/2006 | Nayak et al. |
| 7,338,802 B2 | 3/2008 | Frischauf et al. |
| 7,421,316 B2 | 9/2008 | Gray et al. |
| 7,556,611 B2 | 7/2009 | Kolenbrander et al. |
| 7,993,297 B2 | 8/2011 | Vinci et al. |
| 8,075,468 B2 | 12/2011 | Min et al. |
| 8,235,931 B2 | 8/2012 | Burbank et al. |
| 8,753,515 B2 | 6/2014 | Curtis et al. |
| 8,852,140 B2 | 10/2014 | Barry, Jr. et al. |
| 2012/0118801 A1* | 5/2012 | Rada ............... A61M 1/342 210/137 |
| 2012/0132574 A1 | 5/2012 | Ware et al. |
| 2012/0310135 A1 | 12/2012 | Bauer et al. |
| 2013/0008854 A1 | 1/2013 | Wallace et al. |
| 2013/0338559 A1 | 12/2013 | Franano et al. |
| 2014/0291243 A1 | 10/2014 | Curtis et al. |

FOREIGN PATENT DOCUMENTS

| | | |
|---|---|---|
| EP | 1458431 B1 | 1/2009 |
| EP | 1357958 B1 | 8/2010 |
| EP | 2289577 A1 | 3/2011 |
| EP | 2476447 A1 | 7/2012 |
| EP | 2442847 B1 | 8/2013 |
| EP | 1129291 B1 | 12/2014 |
| WO | WO 95/10310 | 4/1995 |
| WO | WO 01/18396 A1 | 3/2001 |
| WO | WO 03/011376 A2 | 2/2003 |
| WO | WO 03/055542 A1 | 7/2003 |
| WO | WO 2004/066121 A2 | 8/2004 |
| WO | WO 2005/039671 A2 | 5/2005 |
| WO | WO 2007/133259 A1 | 11/2007 |
| WO | WO 2010/025826 A2 | 3/2010 |
| WO | WO 2010/146342 A2 | 12/2010 |
| WO | WO 2011/068885 A1 | 6/2011 |
| WO | WO 2012/163516 A1 | 12/2012 |

* cited by examiner

SYSTEMS AND METHODS FOR REAL TIME CALIBRATION OF PUMP STROKE VOLUMES DURING A BLOOD SEPARATION PROCEDURE

BACKGROUND

Field of the Disclosure

The invention relates to fluid separation systems and methods. More particularly, the invention relates to systems employing spinning membranes for fluid separation and methods for operating such systems.

Description of Related Art

Various blood processing systems now make it possible to collect particular blood constituents, instead of whole blood, from a blood source such as, but not limited to, a container of previously collected blood or other living or non-living source. Typically, in such systems, whole blood is drawn from a blood source, a particular blood component or constituent is separated, removed, and collected, and the remaining blood constituents are returned to the blood source. Removing only particular constituents is advantageous when the blood source is a human donor, because potentially less time is needed for the donor's body to return to pre-donation levels, and donations can be made at more frequent intervals than when whole blood is collected. This increases the overall supply of blood constituents, such as plasma and platelets, made available for transfer and/or therapeutic treatment.

Whole blood is typically separated into its constituents (e.g., red cells, platelets, and plasma) through centrifugation, such as in the AMICUS® separator from Fenwal, Inc. of Lake Zurich, Ill., or other centrifugal separation devices, or a spinning membrane-type separator, such as the AUTOPHERESIS-C® and AURORA® devices from Fenwal, Inc. Such separation devices typically comprise a fluid circuit having a separation chamber, sources or containers of various solutions, and collection containers that are interconnected by tubing and which is mounted onto a durable hardware component that includes pumps, clamps, and sensors that are automatically operated by a programmable controller to perform the desired blood separation procedure.

Operation of the system to perform the desired procedure requires control of the fluid flow rates and volumes of fluid circulated through the various components of the fluid circuit. Fluid flow through the fluid circuit is caused by operation of the pumps acting on the tubing segments associated therewith. Flow rates through the tubings caused by the pumps may vary from procedure to procedure, and even during the course of a single procedure, due to factors such as variations in the tubing comprising the fluid circuit, changes in inlet pressure, variations in how the fluid circuit is mounted to the durable hardware component, variations in the characteristics of the biological fluid being processed (such as variations in hematocrit), etc. Given the potential for variation in flow rates and volumes, it is necessary to monitor and, if necessary, adjust the operation of the pumps to insure that the separation procedure is safely and efficiently performed. By way of the present disclosure, systems and methods for calibrating pump stroke volumes during a blood separation procedure are provided.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In a first aspect, a method for real time calibration of a pump stroke volume to achieve a target fluid flow rate is provided where the fluid processing procedure utilizes a tubing set comprising a tubing through which fluid is flowed and a reusable hardware component comprising at least one pump having a stroke volume, a rotational rate, and an inlet through which fluid is flowed by operation of the pump, and a programmable controller. The controller is programmed with a continuous function defining a relationship between pump inlet pressure and pump stroke volume, and the programmable controller controls the fluid processing procedure based at least in part on the fluid flow rate through the pump, the fluid flow rate being the product of the pump stroke volume and the pump rotational rate. In one example, the continuous function defining the relationship between pump inlet pressure and the pump stroke volume may be empirically determined over a predetermined range of inlet pressures.

The method includes the steps of: commencing the fluid processing procedure to operate the pump to draw fluid through the tubing; measuring fluid pressure in the tubing at the inlet of the pump; calculating a current pump stroke volume with the controller based on the continuous function and the pump rotational rate (as provided by feedback from the pump); and adjusting the pump rotational rate utilized by the controller to control the procedure to achieve the target fluid flow rate.

In another aspect of the method, the fluid pressure at the pump inlet is measured at regular intervals during the fluid processing procedure. The regular intervals may be based on a number of pump strokes. Alternatively, the regular intervals may be based on time.

In a further aspect, the fluid processing procedure may be a blood separation procedure, in which case the pump may be a blood pump that is calibrated in accordance with the method during the draw/collection/separation phase of the procedure, and/or during the return phase of the procedure.

In a related aspect, a blood processing system for processing whole blood or a whole blood component is provided in which the processing system comprises at least one pump and a controller with a user interface and has a fluid flow circuit with at least one tubing associated therewith, and the controller is configured to perform the methods of any one, or combination of, the aspects described above.

DESCRIPTION OF THE ILLUSTRATED EMBODIMENTS

The embodiments disclosed herein are for the purpose of providing an exemplary description of the present subject matter. They are, however, only exemplary, and the present subject matter may be embodied in various forms. Therefore, specific details disclosed herein are not to be interpreted as limiting the subject matter as defined in the accompanying claims.

Figure 1:
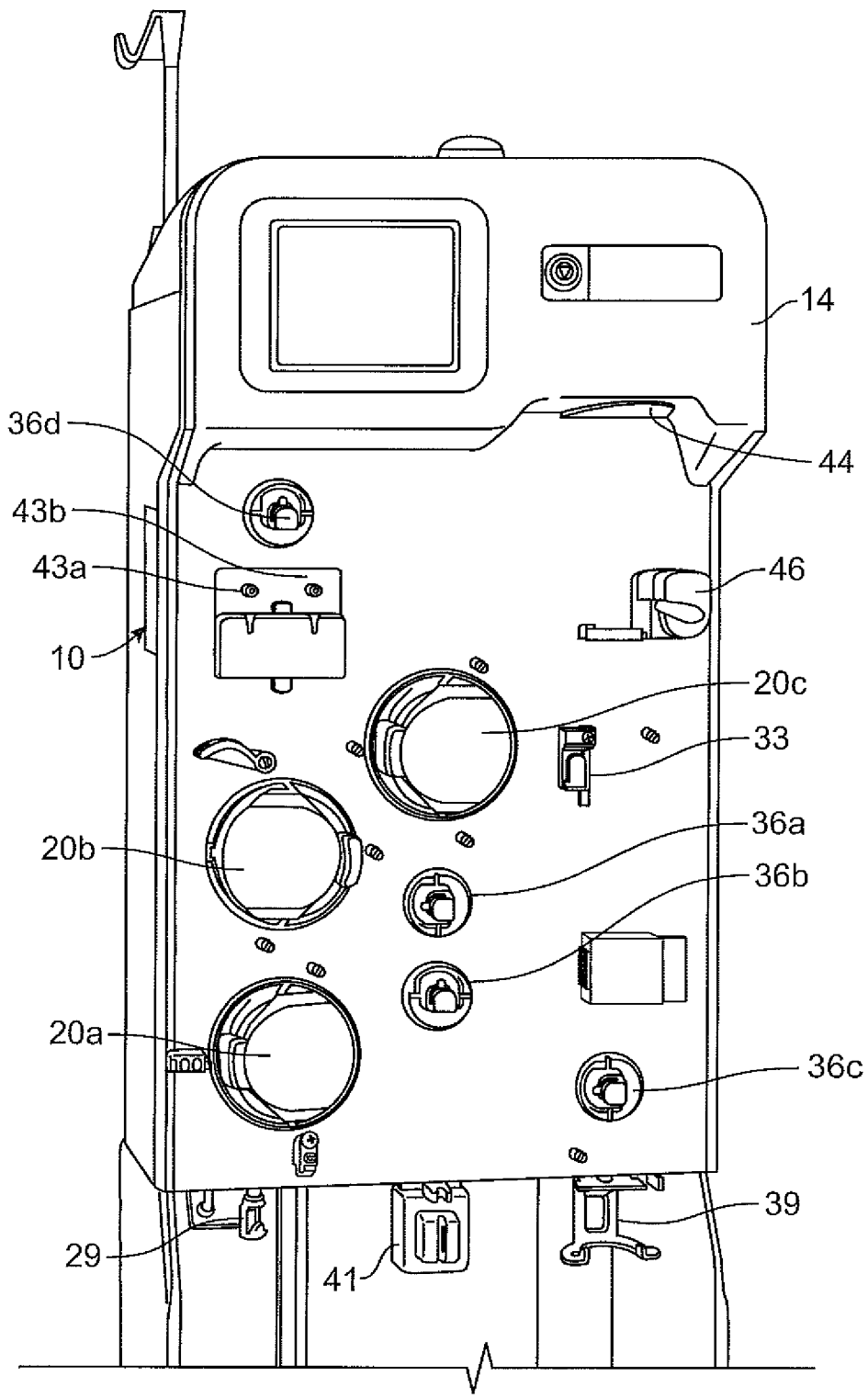
FIG. 1 is a front perspective view of an exemplary fluid separation system suitable for performing the method of the present disclosure.
Figure 2:
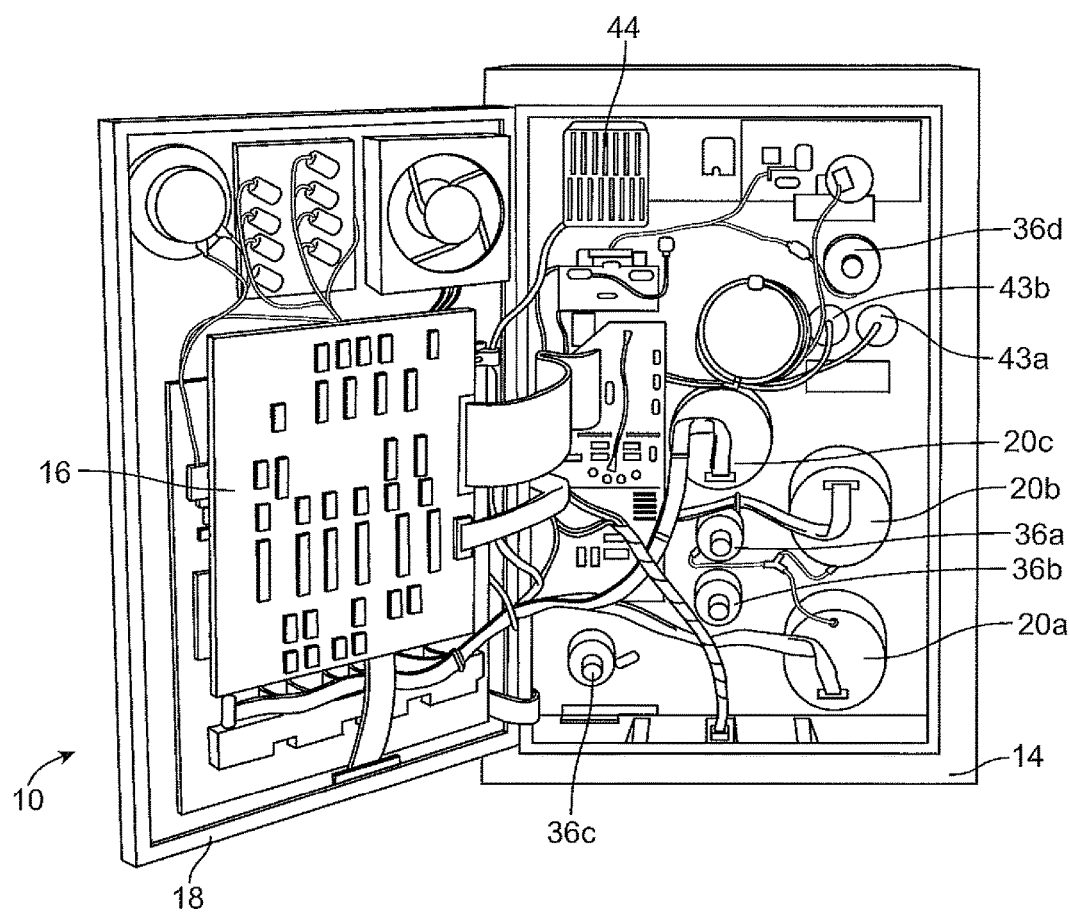
FIG. 2 is a rear perspective view of the fluid separation system of FIG. 1, with a rear door thereof in an open position.
Figure 3:
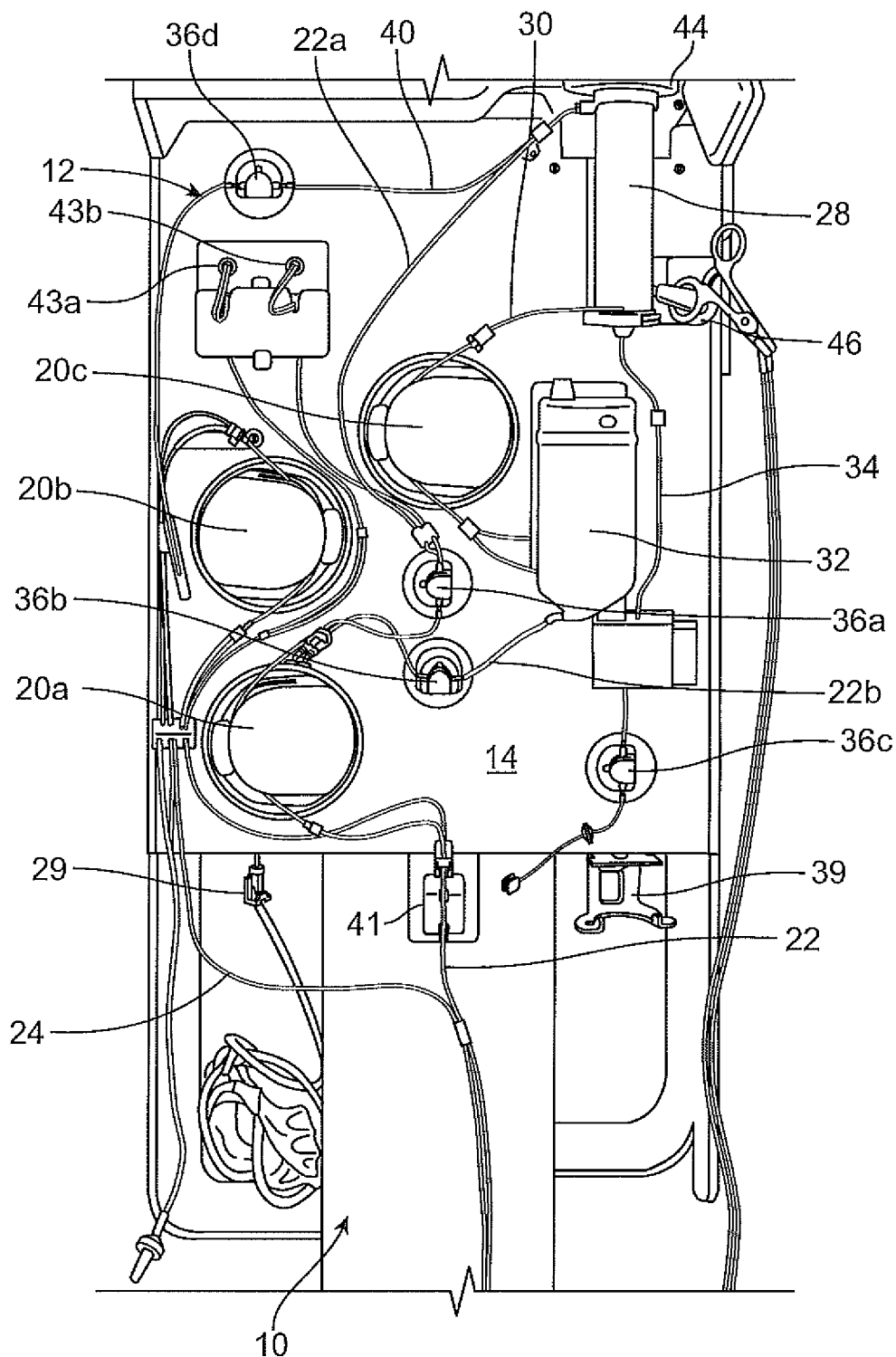
FIG. 3 is a front perspective view of the fluid separation system of FIG. 1, with a fluid flow circuit associated therewith.

According to an aspect of the present disclosure, a durable or reusable fluid separation system is used in combination with a separate fluid flow circuit (which may be disposable) to separate a fluid into two or more constituent parts. FIGS. 1 and 2 illustrate an exemplary fluid separation system 10, while FIG. 3 illustrates an exemplary fluid flow circuit 12 mounted onto the fluid separation system 10, but it should be understood that the illustrated fluid separation system 10 and fluid flow circuit 12 are merely exemplary of such systems and circuits and that differently configured fluid separation systems and fluid flow circuits may be provided without departing from the scope of the present disclosure.

The system 10 of FIG. 1 is configured for processing whole blood, but it may be used to process other biological fluids. The fluid may come from any fluid source during a draw or collection phase of the procedure (see, e.g., FIG. 5) and be returned to any recipient, which may be the same as or different from the fluid source, during a return or reinfusion stage (see, e.g., FIG. 6). In one embodiment, the fluid source/recipient is a living donor or patient (e.g., a human blood donor), while in other embodiments the fluid source and/or fluid recipient may be a non-living source/recipient (e.g., a blood bag or fluid container).

The illustrated system 10 includes a cabinet or housing 14, with several components positioned outside of the cabinet 14 (e.g., associated with a front wall or surface or panel of the cabinet 14) and additional components (including a programmable central processing unit or controller 16 having a plurality or programmable control circuits) and interconnects positioned inside of the cabinet 14, which may be accessed by opening a rear door 18 of the system 10, as shown in FIG. 2. The programmable control circuits are preferably integrated into a single, unitary controller. Among the system components positioned on the outside of the cabinet 14, one or more pumps or pump stations 20a-20c may be provided, with the pumps 20a-20c configured to accommodate tubing lines of the fluid flow circuit 12.

One of the pumps 20a may be provided as a source/recipient access pump, which may be associated with a source/recipient access line 22 of the fluid flow circuit 12 and operates to draw fluid from a fluid source (FIG. 5) during the draw or collection phase, operates in reverse to return fluid to a fluid recipient (FIG. 6) during the reinfusion stage, and is stopped at the end of the reinfusion phase. Pump 20a also primes the fluid flow circuit 12 and clears air from the access line 22. Pump 20a may also be referred to herein as a "blood pump," as it serves to pump whole blood from its source (such as a donor or, in the case of previously collected blood, a container or reservoir) to the separation module or chamber 28, described below. Pump 20a is also used to return the non-targeted blood components.

Another one of the pumps 20b may be provided as an anticoagulant pump, which may be associated with an anticoagulant line 24 of the fluid flow circuit 12 and operates to add anticoagulant from an anticoagulant source or container 26 of the fluid flow circuit 12 (FIG. 5) to fluid drawn from the fluid source in the source/recipient access line 22 before the fluid enters into a fluid separation module or chamber 28 of the fluid flow circuit 12. The anticoagulant container 26 is supported by a weigh scale hanger 29. Pump 20b does not, however, operate during the reinfusion phase of the procedure. Pump 20b may also be referred to herein as an "AC pump."

A third pump 20c may be provided as a return fluid pump, which may be associated with a return fluid outlet line 30 and operates to draw a return fluid (i.e., a fluid constituent to be returned to a fluid recipient) from the fluid separation chamber 28 and direct it into a return fluid reservoir 32 after the fluid has been separated into a return fluid and a collection fluid in the fluid separation chamber 28. The return fluid reservoir is supported by the weigh scale hanger 33. The pump 20c may also be used to prime the fluid flow circuit 12 and assist in clearing fluid from the fluid separation module 28 at the end of the procedure. Pump 20c does not, however, operate during the reinfusion phase of the procedure. Pump 20c may also be referred to herein as a "cell pump," as it serves to deliver cellular concentrate (i.e., concentrated red blood cells) to the return fluid reservoir 32 in a plasmapheresis procedure.

In the illustrated embodiment, the pumps 20a-20c are peristaltic pumps, but it is within the scope of the present disclosure for differently configured pumps, such as diaphragm or other pumps, to be provided. Furthermore, additional or alternative pumps may be provided without departing from the scope of the present disclosure. For example, a pump may be associated with a collection fluid outlet line 34 of the fluid flow circuit 12 to draw a collection fluid from the fluid separation chamber 28 after the fluid from the fluid source has been separated into a return fluid and a collection fluid. Also, as will be described in greater detail herein, the illustrated embodiment employs a single fluid flow tubing or flow path for both drawing fluid from a source and flowing or returning it to a recipient, which are carried out intermittently. The system 10 could employ separate draw and return flow paths or tubes without departing from the scope of the present disclosure.

In addition to the pumps 20a-20c, the external components of the system 10 may include one or more clamps or valves 36a-36d associated with the tubing lines of the fluid flow circuit 12. The clamps or valves 36a-36d may be variously configured and operate to selectively allow and prevent fluid flow through the associated tubing line. In the illustrated embodiment, one clamp or valve 36a may be provided as a fluid source/recipient clamp, which may be associated with a draw branch 22a of the source/recipient access line 22 of the fluid flow circuit 12 to allow (FIG. 5) or prevent (FIG. 6) the flow of fluid through the draw branch 22a of the source/recipient access line 22. Another one of the clamps or valves 36b may be provided as a reinfusion clamp or valve, which may be associated with a reinfusion branch 22b of the source/recipient access line 22 downstream of a return fluid reservoir 32 of the fluid flow circuit 12 to allow (FIG. 6) or prevent (FIG. 5) the flow of return fluid through the reinfusion branch 22b. A third clamp or valve 36c may be provided as a collection fluid clamp or valve, which may be associated with the collection fluid outlet line 34 to allow (FIG. 5) or prevent (FIG. 6) the flow of collection fluid through the collection fluid outlet line 34 and into a collection fluid container 38, which is supported by the weigh scale hanger 39. A fourth clamp or valve 36d may be provided as a replacement fluid clamp or valve, which may be associated with a replacement fluid line 40 of the fluid flow circuit 12 to allow or prevent the flow of a replacement fluid out of a replacement fluid source 42 (e.g., a bag or container at least partially filled with saline). Additional or alternative clamps or valves may also be provided without departing from the scope of the present disclosure.

The illustrated system 10 further includes one or more pressure sensors 43a and 43b that may be associated with the fluid flow circuit 12 to monitor the pressure within one or more of the tubing lines of the fluid flow circuit 12 during operation of the pumps 20a-20c and clamps or valves 36a-36d. In one embodiment, one pressure sensor 43a may be associated with a tubing line that draws fluid from a fluid source and/or directs processed fluid to a fluid recipient, while the other pressure sensor 43b may be associated with a tubing line that directs fluid into or out of the fluid separation chamber 28 to assess the pressure within the fluid separation chamber 28, but the pressure sensors 43a and 43b may also be associated with other tubing lines without departing from the scope of the present disclosure. The pressure sensors 43a and 43b may send signals to the system controller 16 that are indicative of the pressure within the tubing line or lines being monitored by the pressure sensor 43a, 43b. If the controller 16 determines that an improper pressure is present within the fluid flow circuit 12 (e.g., a high pressure due to an occlusion of one of the tubing lines), then the controller 16 may instruct one or more of the pumps 20a-20c and/or one or more of the clamps or valves 36a-36d to act so as to alleviate the improper pressure condition (e.g., by reversing the direction of operation of one of the pumps 20a-20c and/or opening or closing one of the clamps or valves 36a-36d). Additional or alternative pressure sensors may also be provided without departing from the scope of the present disclosure. In addition, the system 10 preferably includes an air detector 41 associated with the donor line 22 to provide a signal to the controller 16 when air is detected in the donor line.

Figure 4:
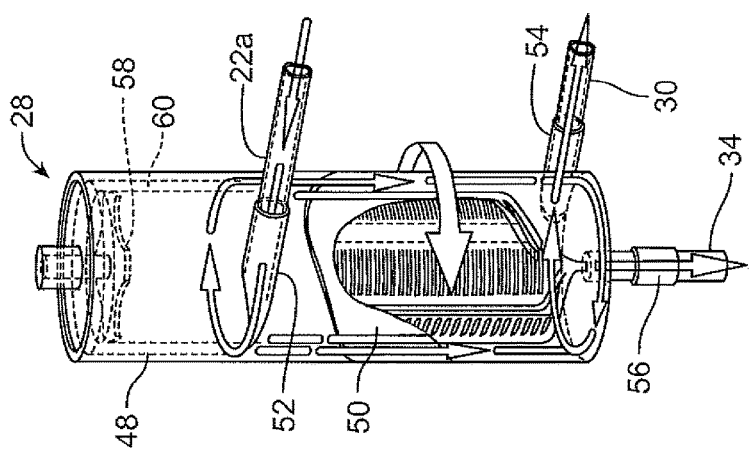
FIG. 4 is a front perspective view of a fluid separation chamber of the fluid flow circuit of FIG. 3, with a portion thereof broken away for illustrative purposes.

The system 10 may also include a separation actuator 44 that interacts with a portion of the fluid separation chamber 28 to operate the fluid separation chamber 28. A chamber lock 46 may also be provided to hold the fluid separation chamber 28 in place with respect to the system cabinet 14 and in engagement with the separation actuator 44. The configuration and operation of the separation actuator 44 depends upon the configuration of the fluid separation chamber 28. In the illustrated embodiment, the fluid separation chamber 28 is provided as a spinning membrane-type separator, such as a separator of the type described in greater detail in U.S. Pat. Nos. 5,194,145 and 5,234,608 or in PCT Patent Application Publication No. WO 2012/125457 A1, each of which is incorporated herein by reference. If provided as a spinning membrane-type separator, the fluid separation chamber 28 may include a tubular housing 48 (FIG. 4), with a microporous membrane 50 positioned therein. An inlet 52 allows a fluid from a fluid source to enter into the housing 48 (via the draw branch 22a of the source/recipient access line 22), while a side outlet 54 allows return fluid to exit the housing 48 (via the return fluid outlet line 30) and a bottom outlet 56 allows collection fluid to exit the housing 48 (via the collection fluid outlet line 34) after the fluid from the fluid source has been separated into return fluid and collection fluid.

In the illustrated embodiment, the separation actuator 44 is provided as a driver that is magnetically coupled to a rotor 58 on which the membrane 50 is mounted, with the separation actuator 44 causing the rotor 58 and membrane 50 to rotate about the central axis of the housing 48. The rotating rotor 58 and membrane 50 create Taylor vortices within a gap 60 between the housing 48 and the membrane 50, which tend to transport the return fluid away from the membrane 50 to exit the fluid separation chamber 28 via the side outlet 54, while the collection fluid passes through the membrane 50 toward the central axis of the housing 48 to exit the fluid separation chamber 28 via the bottom outlet 56. In one embodiment, whole blood from a blood source is separated into cellular blood components (return fluid) and substantially cell-free plasma (collection fluid). It should be understood that the present disclosure is not limited to a particular fluid separation chamber and that the illustrated and described fluid separation chamber 28 is merely exemplary. For example, in other embodiments, a differently configured spinning membrane-type fluid separation chamber may be employed (e.g., one in which the membrane 50 is mounted on an inside surface of the housing 48 or on both the rotor 58 and an inside surface of the housing 48 and facing the gap 60) without departing from the scope of the present disclosure.

The membrane 50 of the fluid separation chamber 28 may be variously configured without departing from the scope of the present disclosure. When the system 10 is to be used to separate blood into two or more constituents, at least a portion of the membrane 50 preferably has anti-thrombogenic characteristics to prevent or at least decrease the incidence of reaction, such as protein or platelet activation upon the blood being separated within the fluid separation chamber 28. As used herein, the term "anti-thrombogenic" is intended to refer to a substance or property characterized by an enhanced resistance to the accumulation of blood components than the materials typically employed in the manufacture of membranes of spinning membrane-type fluid separation chambers (e.g., nylon 6-6).

Any suitable membrane material (or combination of materials) and anti-thrombogenic material (or combination of materials) may be used in manufacturing the membrane 50. In one embodiment, the membrane 50 is formed of a polymeric material (e.g., nylon 6-6, polyethersulfone, polysulfone, polycarbonate, polyvinylidene fluoride, polyamide, or the like), with an anti-thrombogenic material (e.g., polyethylene glycol or any one of the additives or coatings provided by Interface Biologics, Inc. of Toronto, Canada, or the like) incorporated or mixed or blended therein. In another embodiment, the membrane 50 is fully formed from a polymeric material (e.g., nylon, polyethersuflone, polysulfone, polycarbonate, polyvinylidene fluoride, polyamide, or the like) and then an anti-thrombogenic material (e.g., polyethylene glycol, any one of the additives or coatings provided by Interface Biologics, Inc. of Toronto, Canada, or the like) is applied to or coated onto at least a portion of the formed membrane 50.

Figure 5:
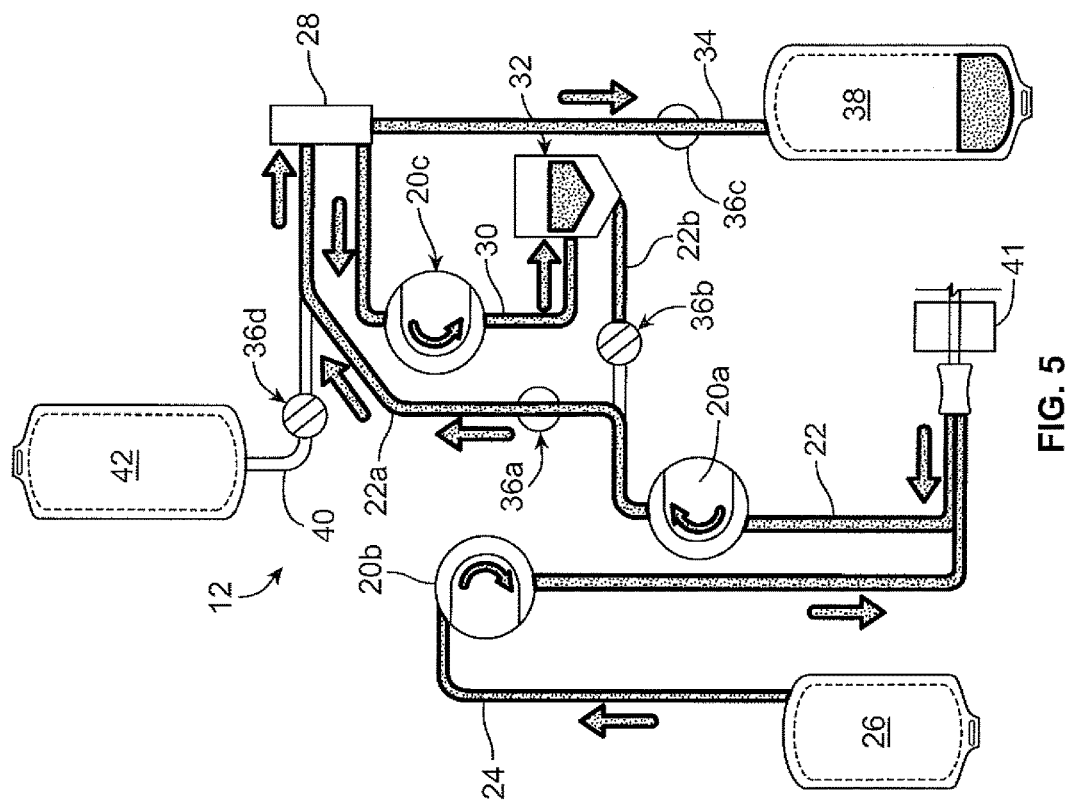
FIG. 5 is a schematic view of the fluid flow circuit and fluid separation system of FIG. 3, in a fluid draw mode.
Figure 6:
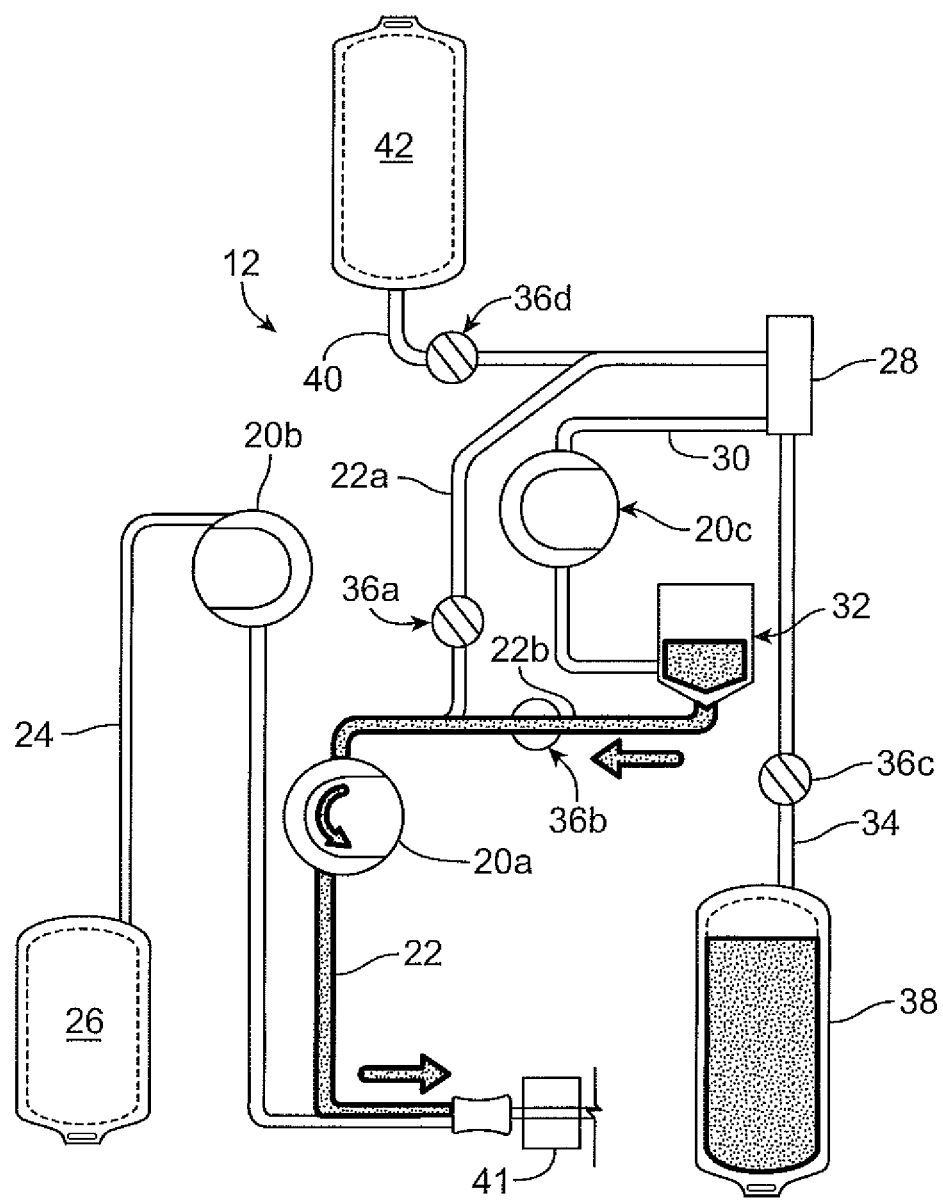
FIG. 6 is a schematic view of the fluid flow circuit and fluid separation system of FIG. 3, in a fluid return mode.

According to one method of using the fluid separation system 10 and fluid flow circuit 12, a fluid is drawn from a fluid source into the fluid separation chamber 28 during a draw or collection phase or mode (FIG. 5), where the fluid is separated into return fluid (e.g., concentrated cellular blood components) and collection fluid (e.g., substantially cell-free plasma). The collection fluid is retained by the system 10, while the return fluid is stored in the reservoir 32 and then returned to the fluid source during a return or reinfusion phase or mode (FIG. 6). In one embodiment, the sequential performance of the draw and return phases (drawing from the fluid source, separating the fluid from the fluid source into return fluid and collection fluid, pumping the collection fluid to the fluid source or a different recipient, and returning the return fluid to the fluid source) are repeated until a target (e.g., a particular amount of collection fluid) is achieved. All of the draw phases and all of the return phases may be identical or may differ from each other. For example, a final draw phase may draw less fluid from the fluid source than the previous draw phases and a final return phase may infuse a combination of return fluid and replacement fluid to the fluid recipient, whereas the previous return phases pump only return fluid to the fluid recipient.

In accordance with the disclosure, a method is provided for the real time calibration of a pump during a blood separation procedure that has a state or phase where fluid is flowed through a tubing segment by action of the pump. The state or phase of the procedure may be a draw state, a collection state, or a separation state, as illustrated in FIG. 5, and/or a return state, as illustrated in FIG. 6, and the pump may be the blood pump 20a.

As contemplated, the steps of the method are preferably automatically implemented by the system controller 16 that controls performance of the procedure based, at least in part, on a fluid flow rate through the fluid circuit 12. Initially, a continuous function defining the relationship between pump inlet pressure and pump stroke volume over a range of inlet pressures is determined, and this relationship is preprogrammed into the controller.

The relationship between pump inlet pressure and pump stroke volume may be determined, either in whole or in part, empirically. For example, the fluid flow rate may obtained by using a fluid separation system 10 to pump fluid through a tubing by means of one of the pumps, such as the blood pump 20a, into a container that is supported by a scale. The inlet pressure to the pump 20a is measured by the pressure sensor 43a, while the pump stroke volume is determining the volume of fluid pumped (based on the change of weight in the container divided by the density of the fluid) and dividing by the number of pump strokes or revolutions, as counted by the controller 16.

Figure 7:
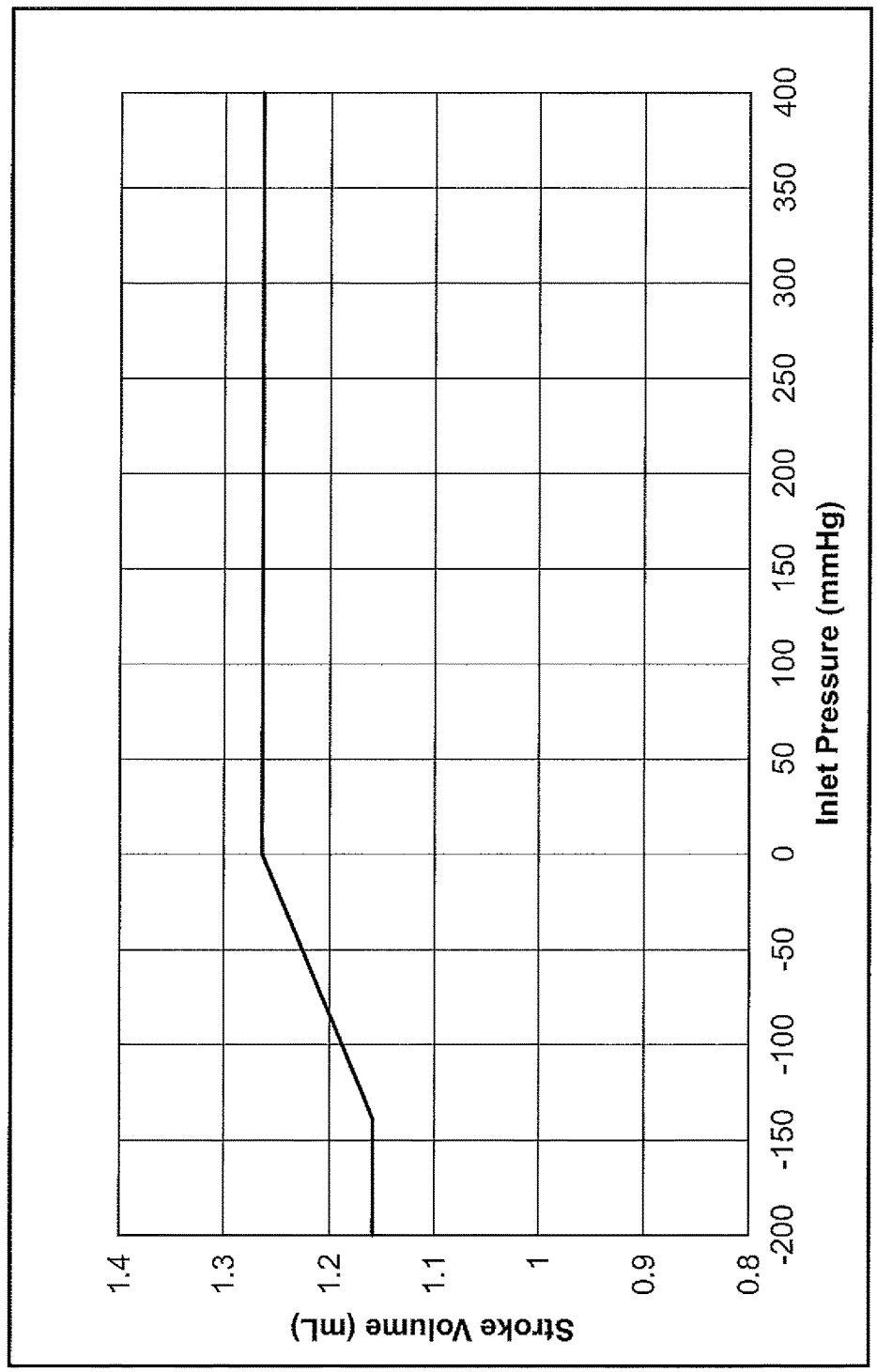
FIG. 7 is a graph of an exemplary empirically-determined relationship between pump inlet pressure and the fluid flow rate through the pump over a predetermined range of inlet pressures in accordance with an aspect of the present disclosure.

Table 1 below reports, for illustrative purposes, experimentally-obtained inlet pressure values in a range of from −140 mmHg to 0 mmHg (the typical operating range for the pump to which the present method is applied) and the corresponding stroke volume in mL, are determined in accordance with the method described above, which is then extrapolated across a range of from −200 mmHg to 400 mmHg as a fixed value corresponding to the nearest tested pressure. This data is plotted in the graph of FIG. 7.

TABLE 1

| Inlet Pressure | Pump Stroke Volume |
| --- | --- |
| −200 | 1.1588 |
| −180 | 1.1588 |
| −160 | 1.1588 |
| −140 | 1.1588 |
| −120 | 1.1735 |
| −100 | 1.1883 |
| −80 | 1.2030 |
| −60 | 1.2178 |
| −40 | 1.2325 |
| −20 | 1.2472 |

TABLE 1-continued

| Inlet Pressure | Pump Stroke Volume |
| --- | --- |
| 0 | 1.2620 |
| 20 | 1.2620 |
| 40 | 1.2620 |
| 60 | 1.2620 |
| 80 | 1.2620 |
| 100 | 1.2620 |
| 120 | 1.2620 |
| 140 | 1.2620 |
| 160 | 1.2620 |
| 180 | 1.2620 |
| 200 | 1.2620 |
| 220 | 1.2620 |
| 240 | 1.2620 |
| 260 | 1.2620 |
| 280 | 1.2620 |
| 300 | 1.2620 |
| 320 | 1.2620 |
| 350 | 1.2620 |
| 400 | 1.2620 |

As can be seen with reference to the data table and graph, the pump stroke volume is substantially constant between −200 and −140, and again between −0− and 400, while it increases in a generally linear manner between −140 and 0. In accordance with the present method, a continuous function defining the plot is derived, and this function is preprogrammed into the controller 16.

Upon commencing the fluid processing procedure, the pump is operated to draw fluid through the tubing, with the controller automatically controlling the performance of the procedure based at least in part on an initial fluid flow rate programmed or input to the controller. This may be the draw/collect/separation phase of a blood separation procedure, in which fluid (whole blood) is flowed through the access line 22 by means of the pump 20a (as illustrated in FIG. 5), and/or a return phase, in which fluid (cell concentrate) is flowed through the access line 22 by means of pump 20a (as illustrated in FIG. 6).

The fluid pressure in the access line 22 at the inlet of the pump 20a is measured by, e.g., the pressure sensor 43a, when fluid is being drawn into the system. The inlet pressure is preferably measured at regular intervals during the performance of the procedure. The intervals may be time-based, so that, e.g., a pressure measurement is taken every 0.1 seconds, or the intervals may be based on, e.g., the operation of the pump, with the pressure measurement being taken every 1 pump stroke.

The controller then calculates a pump stroke volume based on the inlet pressure utilizing the continuous function (obtained, e.g., as described above) that was programmed into the controller. Based on the calculated pump stroke volume, the controller determines the pump rotational rate to achieve the target fluid flow rate for the next time or pumping interval, as described above, and the pump rotational rate utilized by the controller for performing the separation procedure is accordingly.

In keeping with another aspect, the controller may also be preprogrammed with a pump calibration method, such as that described in our co-pending application Ser. No. 14/577,236, incorporated herein by reference, in which the pump stroke volume is adjusted at the start of a subsequent performance of the stage of the procedure based on a change in weight of the reservoirs associated with the preceding performance of the particular stage. In such instances, the real time fluid flow rate obtained by the method described herein is inputted into the second pump calibration method preprogrammed into the controller.

It will be understood that the embodiments and examples described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

Without limiting any of the foregoing, the subject matter herein may be found in one or more methods or apparatus. For example, in a first aspect, a method for real time calibration of the pump stroke volume is provided where the fluid processing procedure utilizes a tubing set comprising a tubing through which fluid is flowed and a reusable hardware component comprising at least one pump having an inlet through which fluid is flowed by operation of the pump, and a controller programmed with a continuous function defining a relationship between pump inlet pressure and the pump stroke volume. The controller controls the fluid processing procedure based at least in part on a fluid flow rate through the pump, the fluid flow rate being the product of the pump stroke volume and the pump rotational rate. The continuous function defining the relationship between pump inlet pressure and the pump stroke volume may be empirically determined over a predetermined range of inlet pressures.

In another aspect, the method includes the steps of: commencing the fluid processing procedure to operate the pump to draw fluid through the tubing; measuring fluid pressure in the tubing at the inlet of the pump; calculating the current pump stroke volume with the controller based on the continuous function and the pump rotational rate; and adjusting the pump rotational rate utilized by the controller to achieve the target fluid flow rate.

In a further aspect of the method, the fluid pressure at the pump inlet is measured at regular intervals during the fluid processing procedure. The regular intervals may be based on a number of pump strokes. Alternatively, the regular intervals may be based on time.

In a further aspect, the fluid processing procedure may be a blood separation procedure, in which case the pump may be a blood pump that is calibrated in accordance with the method during the draw/collection/separation phase and/or the return phase of the procedure, or during the return phase of the procedure.

In a related aspect, a blood processing system for processing whole blood or a whole blood component is provided in which the processing system comprises at least one pump and a controller with a user interface and has a fluid flow circuit with at least one tubing associated therewith, and the controller is configured to perform the methods of any one, or combination of, the aspects described above.

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description, but is set forth in the following claims.

The invention claimed is:

1. In a blood separation procedure having sequentially-performed draw and return phases including at least a first and a second draw phase separated by a first return phase, the procedure utilizing a tubing set comprising a tubing through which fluid is flowed and a reusable hardware component comprising at least one pump having a stroke volume, a rotational rate, and an inlet through which fluid is flowed by operation of the pump and a programmable controller for automatically performing the fluid processing procedure based at least in part on a fluid flow rate through the pump, the fluid flow rate being a product of the pump stroke volume and the pump rotational rate, a method for real time calibration of the pump stroke volume to achieve a target fluid flow rate comprising:
   a) programming the controller with first and second continuous functions defining a relationship between pump inlet pressure and pump stroke volume for each of the draw phase and the return phase;
   b) commencing the first draw phase of the blood separation procedure to operate the pump to draw blood through the tubing;
   c) measuring fluid pressure in the tubing at the inlet of the pump;
   d) calculating a current pump stroke volume for the first draw phase with the controller based on the continuous function for the draw phase and the pump rotational rate;
   e) determining an adjusted pump rotational rate utilized by the controller to control the procedure to achieve the target fluid flow rate;
   f) conforming the pump rotational rate to the adjusted pump rotational rate;
   g) upon completion of the first draw phase, commencing the first return phase; and
   h) upon completion of the first return phase, commencing the second draw phase.

2. The method of claim 1 wherein the relationship between pump inlet pressure and the pump stroke volume is determined empirically over a predetermined range of inlet pressures.

3. The method of claim 1 further comprising measuring the fluid pressure at the pump inlet at regular intervals during the fluid processing procedure.

4. The method of claim 3 wherein the regular intervals are based on a number of pump strokes.

5. The method of claim 3 wherein the regular intervals are based on time.

6. In a blood separation procedure having sequentially-performed draw and return phases including at least a first and a second draw phase separated by a first return phase, the procedure utilizing a tubing set comprising a tubing through which fluid is flowed and a reusable hardware component comprising at least one pump having a stroke volume, a rotational rate, and an inlet through which fluid is flowed by operation of the pump and a programmable controller for automatically performing the fluid processing procedure, wherein the controller is programmed with first and second continuous functions defining a relationship between pump inlet pressure and pump stroke volume for each of the draw phase and the return phase, and the controller controls the separation procedure based at least in part on a fluid flow rate through the pump, the fluid flow rate being a product of the pump stroke volume and the pump rotational rate, a method for real time calibration of the pump stroke volume to achieve a target fluid flow rate comprising:

a) commencing the first draw phase of the blood separation procedure to operate the pump to draw blood through the tubing;
b) measuring fluid pressure in the tubing at the inlet of the pump;
c) calculating a current pump stroke volume and pump rotational rate for the first draw phase with the controller based on the continuous function for the draw phase and the pump rotational rate;
d) determining an adjusted pump rotational rate utilized by the controller to control the procedure to achieve the target fluid flow rate;
e) conforming the pump rotational rate to the adjusted pump rotational rate;
f) upon completion of the first draw phase, commencing the first return phase; and
g) upon completion of the first return phase, commencing the second draw phase.

7. The method of claim 6 wherein the relationship between pump inlet pressure and the pump stroke volume is determined empirically over a predetermined range of inlet pressures.

8. The method of claim 6 further comprising measuring the fluid pressure at the pump inlet at regular intervals during the fluid processing procedure.

9. The method of claim 8 wherein the regular intervals are based on a number of pump strokes.

10. The method of claim 8 wherein the regular intervals are based on time.

11. The method of claim 1 wherein the real time calibration method is used in conjunction with a second pump calibration method programmed into the controller different from the real time calibration method.

12. A blood processing system for processing whole blood or a whole blood component, the processing system comprising at least one pump and a controller with a user interface and having a fluid flow circuit having at least one tubing associated therewith, the controller being configured to perform the method of claim 1.

13. The method of claim 11 wherein the second pump calibration method is based on a change in weight of reservoirs associated with performance of the first draw stage, and the adjusted pump rotational rate determined during the first draw phase is inputted into the second method.

14. The method of claim 13 wherein a second return phase is performed after the second draw phase comprising:
  i) measuring fluid pressure in the tubing at the inlet of the pump during the first return phase;
  j) calculating a current pump stroke volume for the first return phase with the controller based on the continuous function for the return phase;
  k) determining an adjusted pump rotational rate to be utilized by the controller; and
  l) upon completion of the second draw phase, commencing the second return phase using the adjusted pump rotational rate determined during the first return phase and the second pump calibration method.

15. The method of claim 1 wherein the pump is operated in a first direction during each draw phase and in a second direction opposite to the first direction in the first return phase.

* * * * *